(12) United States Patent
Jones et al.

(10) Patent No.: US 11,020,131 B2
(45) Date of Patent: Jun. 1, 2021

(54) MULTI-USE TOOL

(71) Applicant: Zimmer, Inc., Warsaw, IN (US)

(72) Inventors: Nolan C. Jones, Warsaw, IN (US); Shanon N. Roberts, Columbia City, IN (US); Nick Drury, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 248 days.

(21) Appl. No.: 15/782,392

(22) Filed: Oct. 12, 2017

(65) Prior Publication Data
US 2018/0103966 A1 Apr. 19, 2018

Related U.S. Application Data

(60) Provisional application No. 62/408,262, filed on Oct. 14, 2016.

(51) Int. Cl.
*A61B 17/17* (2006.01)
*B23B 31/107* (2006.01)
(Continued)

(52) U.S. Cl.
CPC ........ *A61B 17/1764* (2013.01); *A61B 17/157* (2013.01); *A61B 17/162* (2013.01);
(Continued)

(58) Field of Classification Search
CPC ... A61B 17/1764; A61B 17/157; A61B 17/92; A61B 17/155; A61B 17/8872;
(Continued)

(56) References Cited

U.S. PATENT DOCUMENTS

| 5,308,350 A | * | 5/1994 | Mikhail | A61B 17/02 606/53 |
| 7,424,841 B2 | * | 9/2008 | Liu | B25B 15/001 279/22 |

(Continued)

FOREIGN PATENT DOCUMENTS

| CN | 109803594 A | 5/2019 |
| WO | 2018071693 | 4/2018 |

OTHER PUBLICATIONS

"International Application Serial No. PCT/US2017/056374, International Search Report dated Jan. 25, 2018", 5 pgs.

(Continued)

*Primary Examiner* — Marcela I. Shirsat
(74) *Attorney, Agent, or Firm* — Schwegman Lundberg & Woessner, P.A.

(57) ABSTRACT

Apparatuses and systems including an instrument for manipulating components within a knee joint of a patient are disclosed. Such manipulation can include inserting and/or removing such components to or from a bone of the knee joint. The instrument can include a handle, a body, a plunger, a detent and a collar. The handle can have a proximal end and a distal end and a longitudinal extent between the proximal end and the distal end. The body can be coupled to the handle and can extend distal of the distal end. The body can define a receptacle therein having an opening at a distal end portion of the instrument. The plunger can be moveably disposed within the body and can be moveable between a first position and a second position. The detent can be moveable by the plunger, such that with the plunger in the first position at least a portion of the detent can extend into the receptacle and with the plunger in the second position the detent can be recessed from the receptacle. The collar can be disposed about at least a portion of the body and can be (Continued)

moveable relative to the body to operatively actuate the plunger from the first position to the second position.

14 Claims, 9 Drawing Sheets

(51) Int. Cl.
| | |
|---|---|
| *A61F 2/46* | (2006.01) |
| *A61B 17/16* | (2006.01) |
| *A61B 17/92* | (2006.01) |
| *A61B 17/15* | (2006.01) |
| *A61B 17/00* | (2006.01) |
| *A61B 17/88* | (2006.01) |

(52) U.S. Cl.
CPC .............. *A61B 17/92* (2013.01); *A61F 2/461* (2013.01); *B23B 31/1071* (2013.01); *A61B 17/155* (2013.01); *A61B 17/8872* (2013.01); *A61B 2017/00464* (2013.01); *A61B 2017/00473* (2013.01); *A61B 2017/924* (2013.01); *A61B 2017/927* (2013.01); *A61F 2/4603* (2013.01)

(58) Field of Classification Search
CPC ........ A61B 2017/924; A61B 2017/927; A61B 2017/928; A61B 2017/0046; A61B 2017/00464; A61B 2017/00473; A61B 2017/00477; A61F 2/4603; A61F 2/461; A61F 2002/4619; A61F 2002/4623; A61F 2002/4624; A61F 2002/4625; B23B 31/107; B23B 31/1071; B25G 1/00; B25G 1/10; B25G 1/102
USPC .......... 606/86 R, 87–88, 89, 99, 86 A, 86 B; 623/22.12; 81/489, 177.1; 269/3, 6
See application file for complete search history.

(56) References Cited

U.S. PATENT DOCUMENTS

| | | |
|---|---|---|
| 7,810,817 B1 | 10/2010 | Gao |
| 2004/0220554 A1 | 11/2004 | Lechot et al. |
| 2012/0253323 A1* | 10/2012 | Bharadwaj ......... A61B 17/8883 606/1 |
| 2014/0114321 A1 | 4/2014 | Davenport et al. |
| 2016/0214240 A1* | 7/2016 | Chen .................. B25B 23/0035 |
| 2017/0007273 A1 | 1/2017 | Freiberg et al. |

OTHER PUBLICATIONS

"International Application Serial No. PCT/US2017/056374, Written Opinion dated Jan. 25, 2018", 6 pgs.
"European Application Serial No. 17791251.6, Response to Communication pursuant to Rules 161(1) and 162 EPC filed Dec. 9, 2019", 18 pgs.
"European Application Serial No. 17791251.6, Communication Pursuant to Article 94(3) EPC dated Apr. 23, 2019", 18 pgs.
"European Application Serial No. 17791251.6, Response filed Aug. 27, 2020 to Communication Pursuant to Article 94(3) EPC dated Apr. 23, 2020", 43 pgs.

* cited by examiner

MULTI-USE TOOL

CLAIM OF PRIORITY

This application claims the benefit of U.S. Provisional Patent Application Ser. No. 62/408,262, filed on Oct. 14, 2016, the benefit of priority of which is claimed hereby, and which is incorporated by reference herein in its entirety.

FIELD

The present subject matter relates to orthopedic procedures and, more particularly, to instruments used in performing knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components, and a unicompartmental knee arthroplasty, where only one damaged compartment of the knee is repaired with prosthetic components.

During a surgical procedure to implant a prosthetic knee joint, a provisional femoral component and a provisional tibial component can be placed on a distal femur and proximal tibia, respectively, after resecting the distal femur and proximal tibia. The provisional components assist with confirming the proper size and position of the permanent femoral and tibial components. The provisional components typically come in a range of sizes representative of the size and shape of the permanent components of the chosen prosthesis system. Provisional components are typically selected after making a preliminary determination of the proper size of the permanent components. A trial reduction of the knee joint with the provisional components in place may indicate that the preliminary size determination was not ideal. Alternative provisional components can then be selected and another trial reduction performed. After determining the proper size components, final prosthesis components are seated. Insertion and extraction of the provisional components and other components such as cut guides and the final prosthesis components can be performed with dedicated instruments.

OVERVIEW

The present inventors recognize, among other things, an instrument that facilitates easier more reliable grasping and manipulation of various tools and prostheses used in knee procedures. The present inventors further recognize that procedures can be simplified and costs reduced by providing a single instrument that can couple with multiple tools and prostheses. Components that can couple with the instrument can include cut guides, spacers and prostheses, for example. More particularly, the present inventors have recognized an instrument that can facilitate insertion and/or extraction of various components to facilitate placement and/or removal of the same during a surgical procedure. As such, the instrument can be configured to a receptacle open along a distal tip and a detent movably disposed within the receptacle to mate with and engage the various tools and components. The detent can be biased to engage with the component to hold the component to the instrument. According to some examples, the instrument can utilize a collar as an actuator to overcome the bias on the detent. Such actuation can be accomplished by moving a plunger via the collar relative to the detent. This movement can allow the detent to be retracted from the receptacle and be received in a recess in the plunger, for example.

To further illustrate the apparatuses and systems disclosed herein, the following non-limiting examples are provided:

Example 1 is an instrument for at least one of mounting and removal of a component to or from bone during a knee procedure, the instrument can comprise: a handle having a proximal end and a distal end and a longitudinal extent between the proximal end and the distal end; a body connected to the handle and extending distal of the distal end, the body defining a receptacle therein having an opening at a distal end portion of the instrument; a plunger moveably disposed within the body and moveable between a first position and a second position; a detent moveable by the plunger such that with the plunger in the first position, at least a portion of the detent extends into the receptacle, and with the plunger in the second position the detent is recessed from the receptacle; and a collar disposed about at least a portion of the body and moveable relative to the body to operatively actuate the plunger from the first position to the second position.

In Example 2, the subject matter of Example 1 optionally can include a spring disposed within the body and configured to apply a force on the plunger that holds the plunger in the first position.

In Example 3, the subject matter of Example 2 optionally can include a pin extending through at least a portion of the collar, the plunger and the body, wherein the pin is contacted by the spring and transfers the force to the plunger.

In Example 4, the subject matter of Example 3 optionally can include at least one of the collar and the body includes one or more slots configured to receive the pin, and wherein the one or more slots are configured to allow proximal and distal travel of the pin relative to the body.

In Example 5, the subject matter of any one or more of Examples 1-4 optionally can include the plunger defines a recess configured to receive the detent therein when the plunger is in the second position and the plunger has a ramp surface from the recess to a nose projection, and wherein the nose projection is configured to hold the at least the portion of the detent within the receptacle when the plunger is in the first position.

In Example 6, the subject matter of any one or more of Examples 1-5 optionally can include the opening of the receptacle is recessed from a distal end of the body.

In Example 7, the subject matter of any one or more of Examples 1-6 optionally can include a distal tip of the body comprises an engagement feature configured to engage the bone and provide a proximal/distal stop for the instrument.

In Example 8, the subject matter of Example 7 optionally can include the engagement feature is configured with curvatures along an engagement face in both a longitudinal direction and a transverse direction.

In Example 9, the subject matter of any one or more of Examples 7-8 optionally can include the instrument is configured to be reversible with respect to a longitudinal axis so as to dispose the engagement feature in a first orientation to make engagement with the bone and a second orientation to avoid contact with the bone.

Example 10 is a system for a knee arthroplasty procedure that can comprise: an instrument that can include: a body defining a receptacle therein having an opening at a distal end portion of the instrument; a plunger moveably disposed within the body and moveable between a first position and a second position; a detent moveable by the plunger, such that with the plunger in the first position at least a portion of the detent extends into the receptacle and with the plunger in the second position the detent is recessed from the receptacle; and a collar disposed about at least a portion of the body and moveable relative to the body to operatively actuate the plunger from the first position to the second position; one or more components configured for insertion into a knee joint during the knee arthroplasty procedure, wherein each of the one or more components have a projection configured to insert in the receptacle of the instrument, the projection further having a recess configured to receive the detent therein to couple the instrument with the one or more components.

In Example 11, the subject matter of Example 10 optionally can include the one or more components include at least one tibial provisional component, at least one femoral resection guide, and at least one femoral spacer block.

In Example 12, the subject matter of any one or more of Examples 10-11 optionally can include the instrument further includes a spring disposed within the body and configured to apply a force on the plunger that holds the plunger in the first position.

In Example 13, the subject matter of Example 12 optionally can include a pin extending through at least a portion of the collar, the plunger and the body, wherein the pin is contacted by the spring and transfers the force to the plunger.

In Example 14, the subject matter of Example 13 optionally can include at least one of the collar and the body includes one or more slots configured to receive the pin, and wherein the one or more slots are configured to allow proximal and distal travel of the pin relative to the body.

In Example 15, the subject matter of any one or more of Examples 10-14 optionally can include the plunger defines a recess configured to receive the detent therein when the plunger is in the second position and the plunger has a ramp surface from the recess to a nose projection, and wherein the nose projection is configured to hold the at least the portion of the detent within the receptacle when the plunger is in the first position.

In Example 16, the subject matter of any one or more of Examples 10-15 optionally can include the opening of the receptacle is recessed from a distal end of the body.

In Example 17, the subject matter of any one or more of Examples 10-16 optionally can include a distal tip the body comprises an engagement feature configured to engage the bone and provide a proximal/distal stop for the instrument.

In Example 18, the subject matter of Example 17 optionally can include the engagement feature is configured with curvatures along an engagement face in both a longitudinal direction and a transverse direction.

Example 19 is an instrument for at least one of mounting and removal of a component to or from bone during a knee procedure, the instrument can comprise: a body comprising a distal part of the instrument, the body defining a receptacle therein having an opening interfacing but recessed from a distal end of the instrument by an engagement feature configured to engage the bone and provide a proximal/distal stop for the instrument; a detent moveable within the body such that with the detent in a first position at least a portion of the detent extends into the receptacle and with the detent in the second position the detent is recessed from the receptacle; and an actuator configured to operatively actuate the detent from the first position to the second position.

In Example 20, the subject matter of Example 19 optionally can include the engagement feature is configured with curvatures along an engagement face in both a longitudinal direction and a transverse direction.

In Example 21, the subject matter of any one or more of Examples 19-20 optionally can include the instrument is configured to be reversible with respect to a longitudinal axis so as to dispose the engagement feature in a first orientation make engagement with the bone and a second orientation to avoid contact with the bone.

In Example 22, the apparatuses or systems of any one or any combination of Examples 1-21 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems that can be used in various knee procedures including a total knee replacement procedure (TKA), a cruciate retaining total knee procedure, a unicompartmental knee replacement procedure, a bicompartmental knee replacement procedure comprised of two unicompartmental knee replacements, a procedure that utilizes a single (total) femoral component and two unicompartmental tibial components, and other types of knee replacement procedures. Because the instruments of the present disclosure is usable with provisional prostheses as well as tools such as resection guides and spacer blocks, the term "component" will be generically used in this document to denote any such prosthesis or tool.

The disclosed devices can include an instrument (sometimes referred to as a tool or multi-use tool herein) for manipulating components within a knee joint of a patient. Such manipulation can include inserting and/or removing such components to or from a bone of the knee joint. The instrument can include a handle, a body, a plunger, a detent and a collar. The handle can have a proximal end and a distal end and a longitudinal extent between the proximal end and the distal end. The body can be coupled to the handle and can extend distal of the distal end. The body can define a receptacle therein having an opening at a distal end portion of the instrument. The plunger can be moveably disposed within the body and can be moveable between a first position and a second position. The detent can be moveable by the plunger, such that with the plunger in the first position at least a portion of the detent can extend into the receptacle and with the plunger in the second position the detent can be recessed from the receptacle. The collar can be disposed about at least a portion of the body and can be moveable relative to the body to operatively actuate the plunger from the first position to the second position. The instrument can reduce surgical time by providing a rapid secure grasping and manipulation of various components with the use of only a single instrument.

Figure 1:
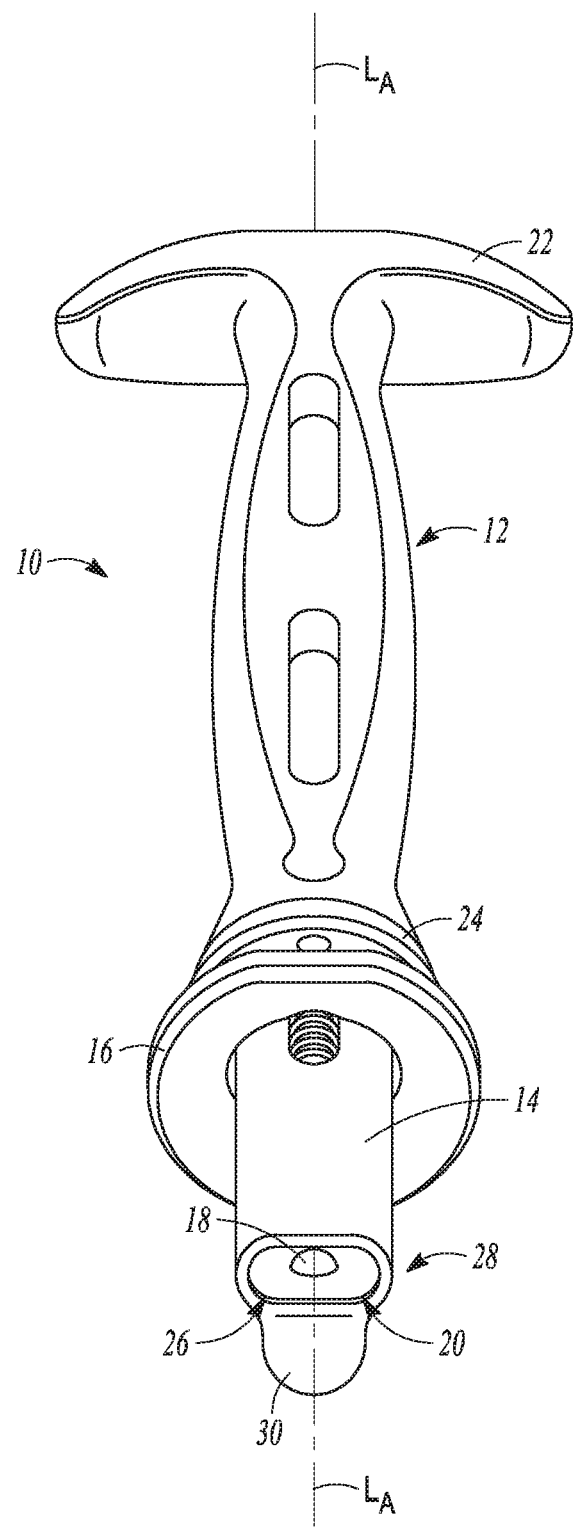
FIG. 1 is a perspective view of instrument having a receptacle at a distal end portion the receptacle including a detent therein according to an example of the present application.

FIG. 1 illustrates an instrument 10 according to one example of the present disclosure. The instrument 10 can include a handle 12, a body 14, a collar 16 and a detent 18. The body 16 can include a receptacle 20.

The instrument 10 can have an elongate shape along a longitudinal axis $L_A$. According to the example of FIG. 1, the handle 12 can be rigidly connected to the body 14. The handle 12 can have a proximal end 22 and a distal end 24 and a longitudinal extent between the proximal end 22 and the distal end 24. The handle 12 can connect to the body 14 at the distal end 24 thereof.

The collar 16 can be disposed about at least a portion of the body 14 and can be located distal of the distal end 24 of the handle 12. The collar 16 can be moveable relative to the body 14 and the handle 12. As will be further discussed, the collar 16 can be movable relative to the body 14 to operatively actuate movement of the detent 18. The detent 18 can comprise a ball detent according to one example, which can be moveably disposed within the body 14. With the detent 18 in a first position (shown in FIG. 1), at least a portion of the detent 18 extends into the receptacle 20. With the detent 18 in the second position (shown in FIGS. 3 and 3A), the detent 18 can be recessed from the receptacle 20.

The body 14 can extend along the longitudinal axis $L_A$ from a proximal connection with the handle 12 adjacent the collar 16. The body 14 can extend distal of the distal end 24 of the handle 12. The body 14 can define the receptacle 20 therein. The receptacle 20 can have an opening 26 at a distal end portion 28 of the instrument 10. More particularly, the opening 26 can be oriented generally transverse to the longitudinal axis $L_A$ such that the opening 26 can face a distal end 30 of the body 14 (the distal end 30 can also comprise a distal end of the instrument 10). As will be discussed subsequently, despite facing the distal end 30 and being disposed at the distal end portion 28, the receptacle 20 and the opening 26 can be recessed along the longitudinal axis $L_A$ from the distal end 30 by a distance. The distance can comprise between 0.1 mm and 4.0 mm according to one example.

Figure 1A:
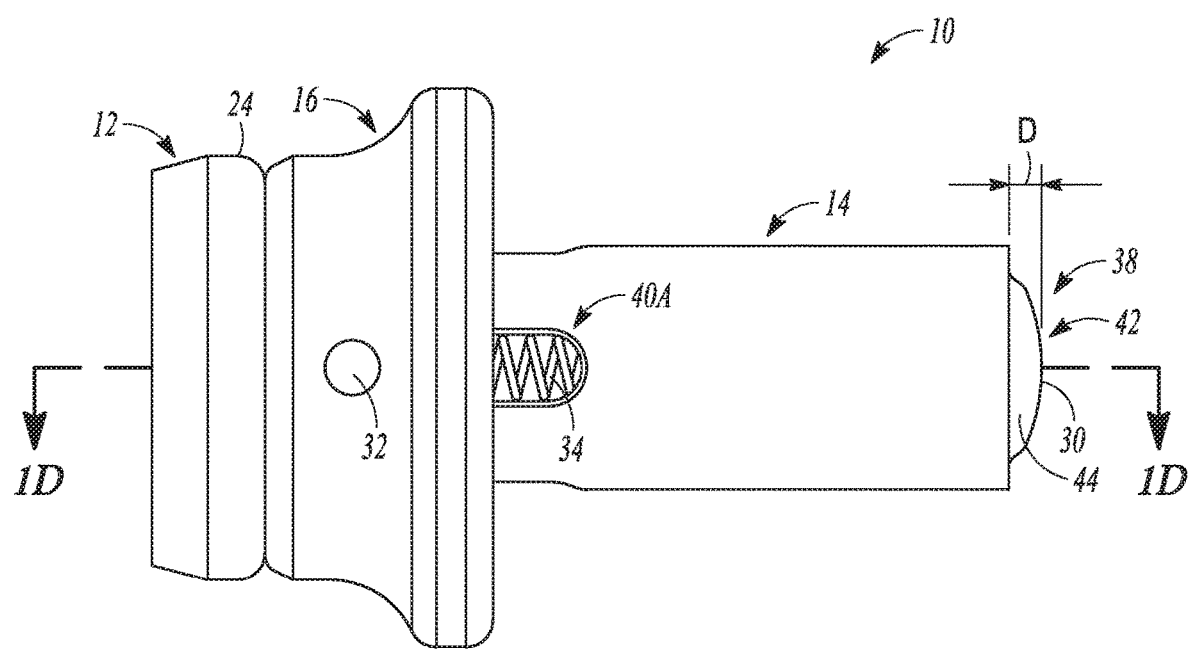
FIG. 1A is a top view of a distal portion of the instrument of FIG. 1 according to an example of the present application.
Figure 1B:
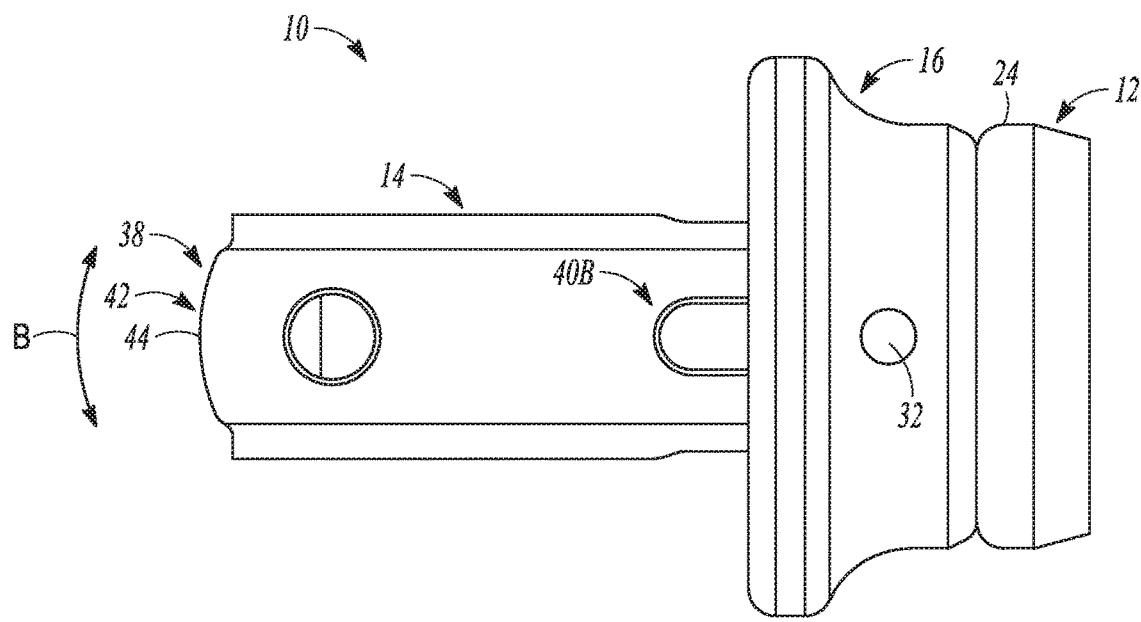
FIG. 1B is a bottom view of the distal portion of the instrument of FIG. 1 according to an example of the present application.
Figure 1C:
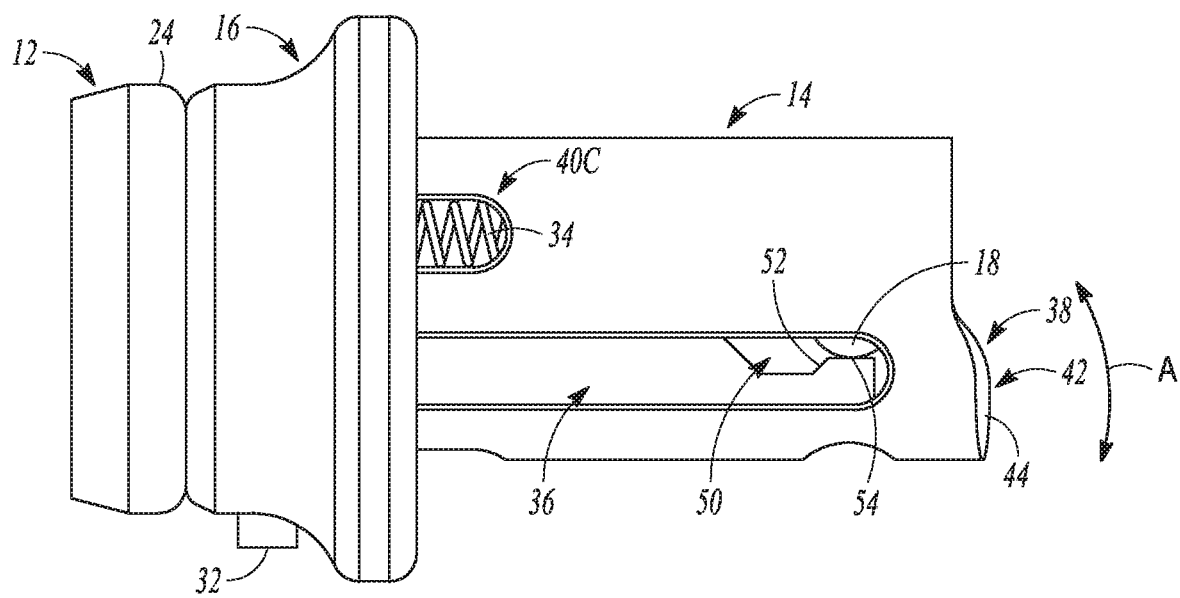
FIG. 1C is a side view of the distal portion of the instrument of FIG. 1 according to an example of the present application.

FIGS. 1A, 1B and 1C comprise enlarged views that further illustrate a portion of the instrument 10 mainly distal of the distal end 24 of the handle 12. As shown in FIGS. 1A-1C, the instrument 10 can include the body 14 and the collar 16 as previously discussed and can further include a pin 32, a spring 34 (FIGS. 1A and 1C), a plunger 36 (FIG. 1C), and a distal tip 38. The body 14 can further define slots 40A (FIG. 1A), 40B (FIG. 1B) and 40C (FIG. 1C). The distal tip 38 can comprise an engagement feature 42.

FIG. 1A shows a first view of the portion of the instrument 10. In FIG. 1A, the pin 32 can be coupled to the collar 16 and can extend through slot 40A. As will be discussed subsequently, the spring 34 can be disposed in the body 14 and can be contacted by the pin 32 at a proximal end. The distal tip 38 of the body 14 can have a curved shape and can extend from the distal end 30 of the body 14 proximally back to the receptacle 20 (FIG. 1). As shown in FIG. 1A, the distal tip 38 can space the distal end 30 of the body 14 a distance D. The distance D can comprise between 0.1 mm and 4.0 mm according to one example.

As shown in FIGS. 1A-1C, the distal tip 38 of the body 14 can comprise the engagement feature 42. The engagement feature 42 can be configured to engage bone and provide a proximal/distal stop for the instrument 10 to position a component on the bone as desired as will be discussed subsequently. As shown in FIGS. 1A-1C, the engagement feature 42 can be configured with curvatures along an engagement face 44 in both a longitudinal direction (indicated by arrow A in FIG. 1C) and a transverse direction (as indicated by arrows B in FIGS. 1B). Thus, the engagement feature 42 can comprise a rounded protrusion with curvatures in one or more directions. Such configuration for the engagement feature 42 can facilitate contact with bone at only one point. This configuration can better accommodate bone variation so that the instrument contacts only a desired bone surface such as an anterior most surface of the tibia, for example. Thus, a desired position of the component on the bone can more easily be achieved.

FIG. 1B shows an opposing side of the instrument 10 from FIG. 1A. The pin 32 can extend through the body 14 and can be coupled to the collar 16 as shown in FIGS. 1A and 1B. The slot 40B can extend longitudinally along the body 14 opposing the slot 40A (FIG. 1A). The slots 40A and 40B can be configured to receive the pin 32 and can be configured to allow proximal and distal travel of the pin 32 relative to the body 14. The pin 32 can be carried by the collar 16 such that actuation of the collar 16 to move proximal/distal can move the pin 32 proximal/distal as well.

Figure 1D:
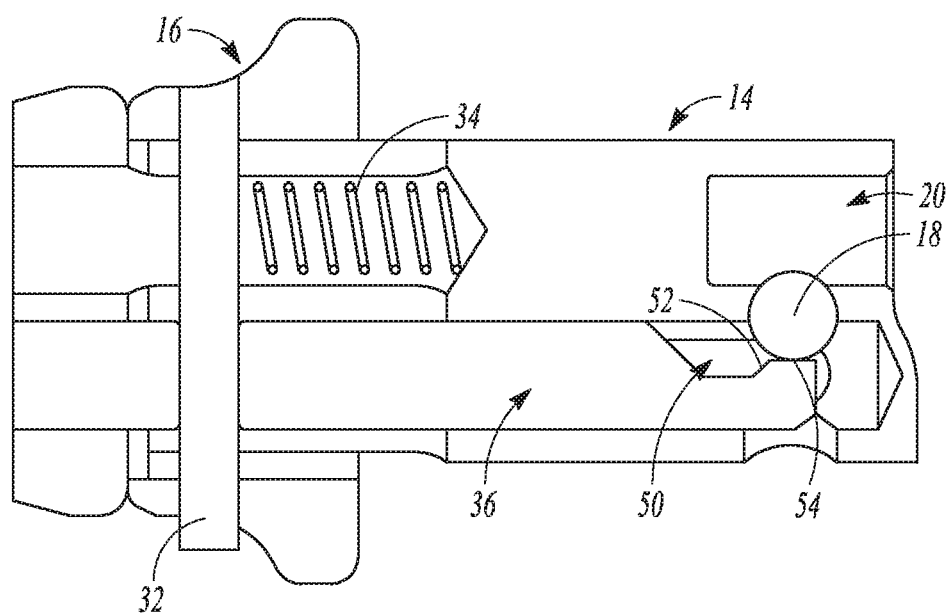
FIG. 1D is a cross-sectional view of the distal portion of the instrument along line 1D-1D of FIG. 1A showing a plunger and the detent in respective first positions according to an example of the present application.

FIGS. 1C and 1D show the spring 34 can be disposed in the body 14 and can contact the pin 32. The plunger 36 can be at least partially disposed in the body 14. In some examples, the plunger 36 can extend distally into the handle 12. The plunger 36 can couple with the pin 32 and can extend distally toward the distal end 30 of the body 14. The plunger 36 can be moveably disposed within the body 14 and can be moveable between a first position (shown in FIGS. 1C and 1D) and a second position (shown in FIGS. 3 and 3A). More particularly, the collar 16 can be coupled to the plunger 36 and moveable relative to the body 14 to operatively actuate the plunger 36 from the first position to the second position.

As shown in FIGS. 1C and 1D, the plunger 36 can define a recess 50 configured to receive the detent 18 therein. The detent 18 can be received in such recess 50 when the plunger 36 is in the second position (shown in FIG. 3A). As shown in FIGS. 1C and 1D, the plunger 36 can have a ramp surface 52 from the recess 50 to a nose projection 54. The nose projection 54 can be configured to hold the at least the portion of the detent 18 within the receptacle 20 as shown in FIG. 1D.

Figure 2:
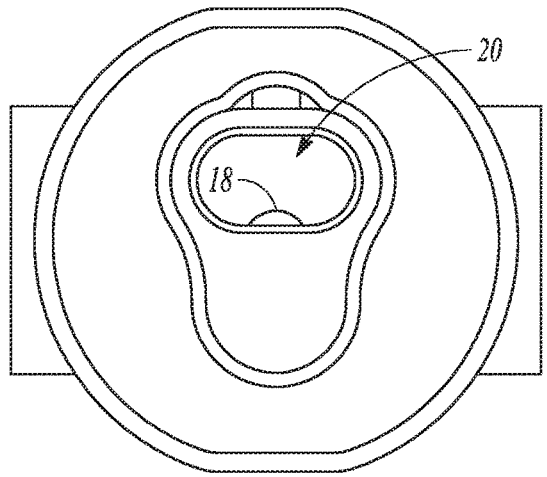
FIG. 2 is an end view of the distal portion of instrument showing an engagement feature and the receptacle with the detent in the first position according to an example of the present application.
Figure 3:
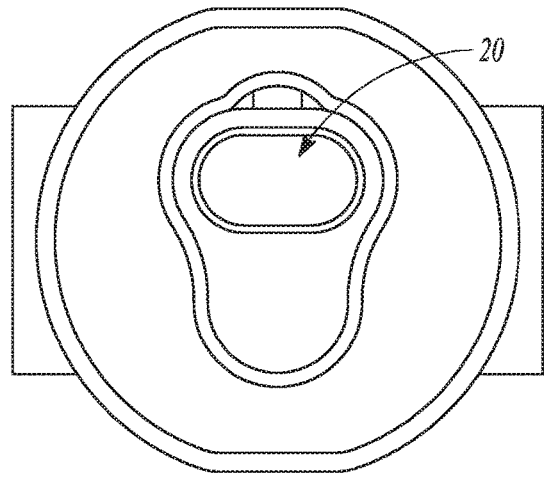
FIG. 3 is an end view of the distal portion of the instrument showing the receptacle with the detent in a second position according to an example of the present application.
Figure 3A:
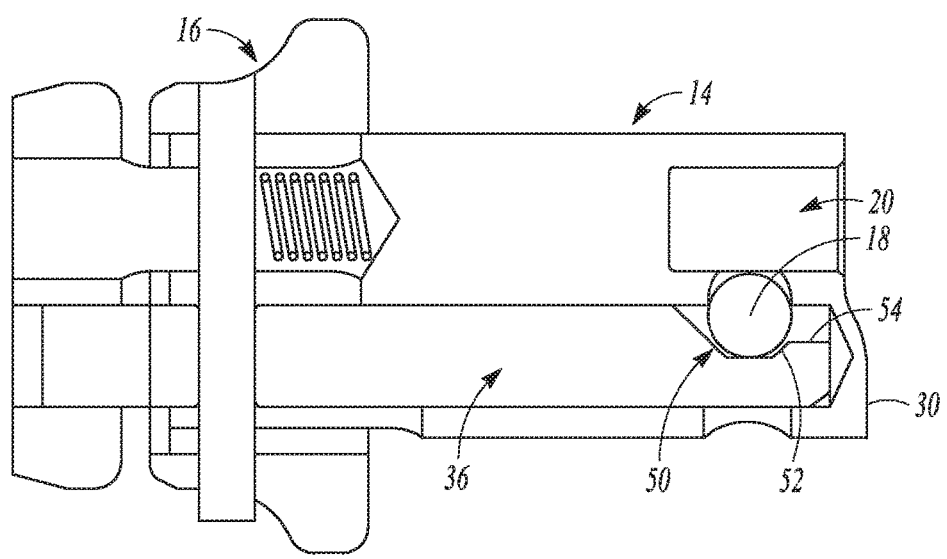
FIG. 3A is a cross-sectional view of the distal portion of the instrument along the same line as FIG. 1D showing the plunger and detent in respective first positions according to an example of the present application.

The detent 18 can be moveable within the body 14 such that with the detent 18 in a first position at least a portion of the detent 18 can extend into the receptacle 20 as shown in FIGS. 1D and 2. With the detent 18 in the second position, the detent 18 can be recessed from the receptacle 20 as shown in FIGS. 3 and 3A. More particularly, the detent 18 can be moveable by the plunger 36 such that with the plunger 36 in the first position, at least a portion of the detent 18 extends into the receptacle 20 as shown in FIG. 1D. With the plunger 36 in the second position, the detent 18 can be recessed from the receptacle 20 as shown in FIG. 3A.

Returning to FIGS. 1C and 1D, the spring 34 can be configured to apply a force on the plunger 36 via the pin 32, which transfers the force to the plunger 36. The force on the plunger 36 can bias the plunger 36 to the first position. To overcome the force of the spring 34, the user can actuate the collar 16 to move the collar 16 distally toward the distal end 30. Such actuation can move the pin 32 and plunger 36 distal allowing the detent 18 to travel down the ramp surface 52 and be received in the recess 50.

FIGS. 3 and 3A show the detent 18 (shown only in FIG. 3A) can be recessed from the receptacle 20 in the second position. More particularly, the FIG. 3A shows the plunger 36 in the second position (where the plunger 36 can be translated relative the body 14 toward the distal end 30 of the body 14 by actuation of the collar 16 and pin 32) where the recess 50 can hold the detent 18, which has traveled down the ramp surface 52 from the nose projection 54.

FIGS. 4A to 7B show various potential uses for the instrument 10 as well as components that can be used with the tool. Each of the various components can be configured for insertion into a knee joint during a knee arthroplasty procedure. Furthermore, each of the components can have a projection configured to insert in the receptacle 20 of the instrument 10. As will be further illustrated in reference to FIGS. 4A to 7B, the projection of each component can further have a recess configured to receive the detent therein to couple the instrument 10 with the component.

Figure 4A:
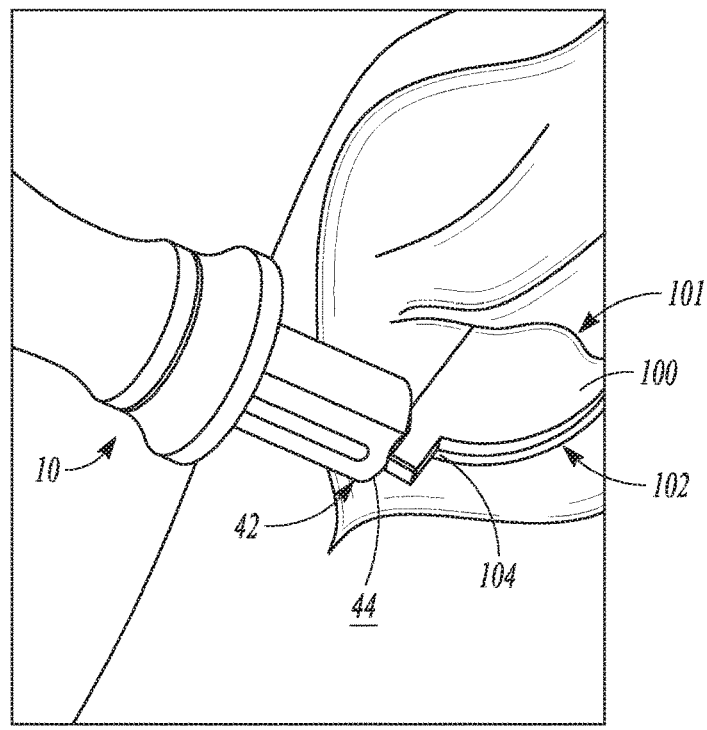
FIG. 4A is a perspective view of the instrument in the process of beginning to engage a tibia of a patient and coupling with a tibial component inserted in the knee joint of a patient according to an example of the present application.

For example, FIG. 4A shows the instrument 10 being positioned and in the process of being coupled to a tibial provisional component 100 within the knee joint 101 of a patient. As previously discussed, the engagement feature 42 of the instrument 100 can be configured to engage bone (tibia 102 in FIG. 4A) and can provide a proximal/distal stop for the instrument 10. As shown in FIG. 4A, the curvature along the engagement face 44 of the engagement feature 42 in one or more directions can facilitate contact with the tibia 102 at only one point along the anterior most surface 104 thereof. The configuration of the engagement feature 42 can better accommodate bone variation so that the instrument 10 can contact the tibia 102 only at a desired bone surface (here the anterior most surface 104 of the tibia 102).

Figure 4B:
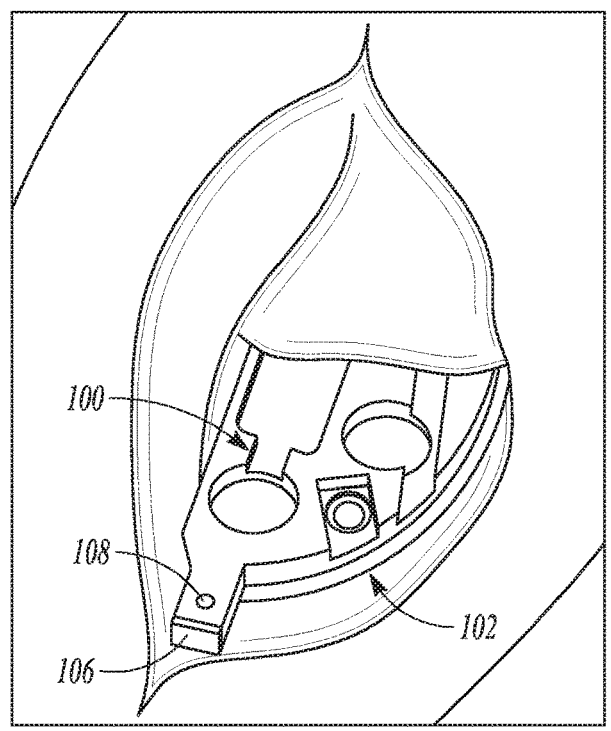
FIG. 4B is a perspective view of the tibial component disposed on the tibia having a coupling feature configured to be received in the receptacle of the instrument according to an example of the present application.

FIG. 4B shows an embodiment of the tibial provisional component 100 disposed on the tibia 102. The tibia provisional component 100 can have a projection 106 configured to insert in the receptacle of the instrument 10 (as shown in FIG. 4A). The projection 106 of the tibial provisional component 100 can define a recess 108 configured to receive the detent 18 (FIG. 1) therein to couple the instrument 10 with the tibial provisional component 100.

Figure 5A:
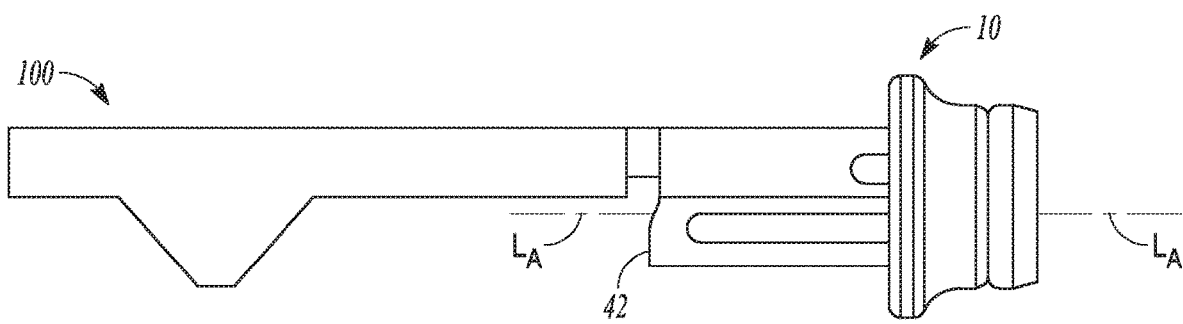
FIG. 5A is a perspective view of the instrument engaging the tibial component with the instrument disposed in a first position according to an example of the present application.
Figure 5B:
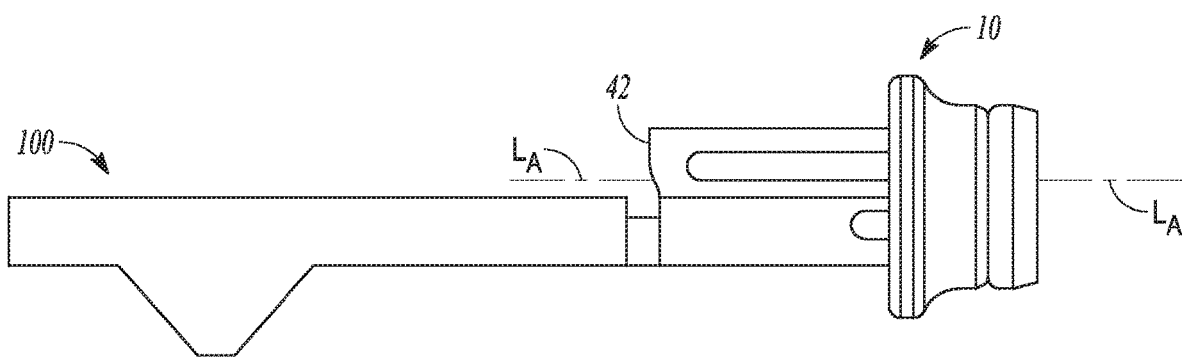
FIG. 5B is a perspective view of the instrument engaging the tibial component with the instrument disposed in a second position according to an example of the present application.

FIG. 5A and 5B show the instrument 10 coupling with the tibial provisional component 100. As shown in FIGS. 5A and 5B, the instrument 10 can be configured to be reversible with respect to a longitudinal axis $L_A$ so as to dispose the engagement feature 42 in a first orientation as shown in FIG. 5A and a second orientation as shown in FIG. 5B. In the first orientation, the engagement feature 42 of the instrument 10 can make engagement with the bone (e.g., the tibia 102 as previously illustrated and described in FIG. 4A). In contrast, the second orientation as shown in FIG. 5B can avoid contact between the engagement feature 42 and the bone. Such non-engagement with the bone may be desirable when coupling the instrument 10 to the tibial provisional component 100 for removing the tibial provisional component 100 from the knee joint. Thus, the likelihood of interference from the bone can be reduced or avoided.

Figure 6A:
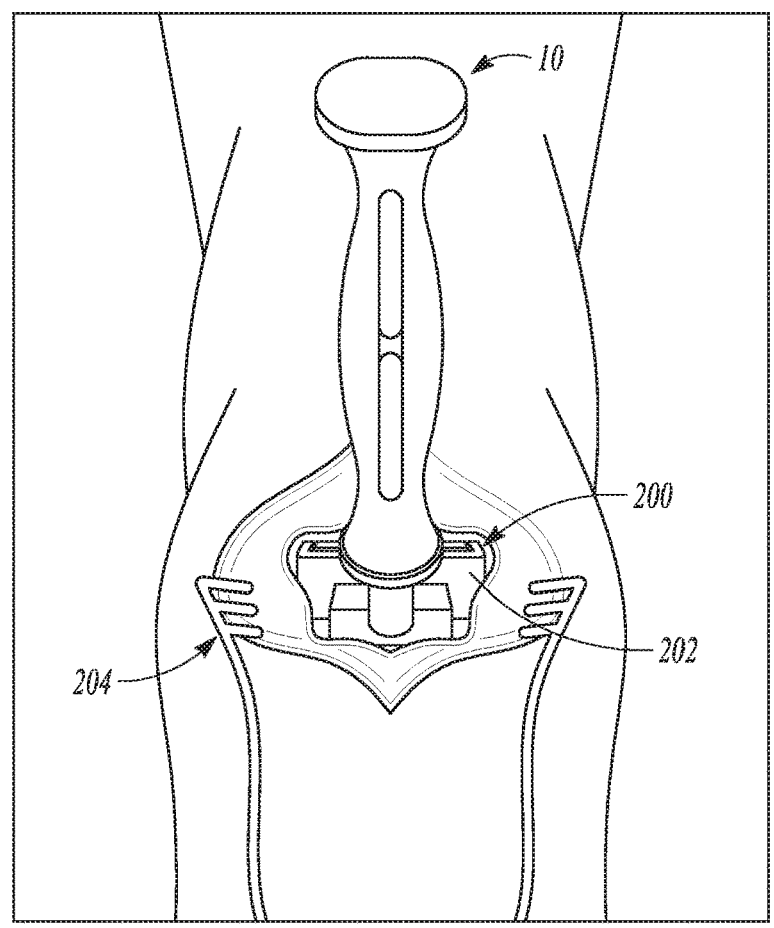
FIG. 6A is a perspective view of the instrument coupling with a femoral distal resection guide and spacer block inserted in the knee joint of a patient according to an example of the present application.
Figure 6B:
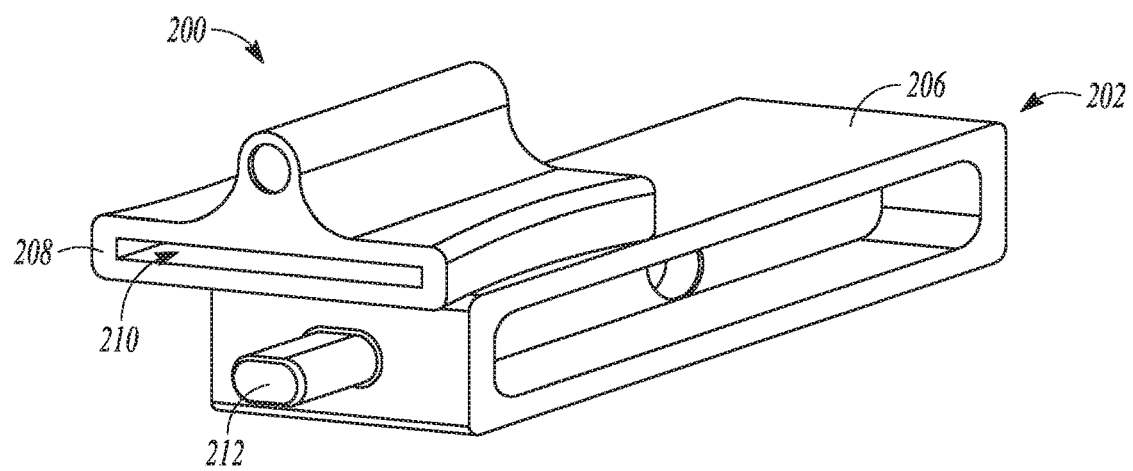
FIG. 6B is a perspective view of the femoral distal resection guide and spacer block having a coupling feature configured to be received in the receptacle of the instrument according to an example of the present application.

FIG. 6A shows the instrument 10 coupling with a second component 200 comprising a guide and spacer block 202 at the knee joint 204 of the patient. With reference to FIG. 6B, the second component 200 comprising the guide and spacer block 202 can comprise a combination of spacer block 206 configured to be inserted between the unresected femur and the resected tibia and a cut guide 208 configured with a cut slot 210 that can aid in resection of the distal portion of the femur.

As shown in FIG. 6B, the second component 200 can have a projection 212 configured to insert in the receptacle of the instrument 10 (as shown in FIG. 6A). The projection 212 of the second component 200 can define a recess (not shown in FIG. 6B) configured to receive the detent 18 (FIG. 1) therein to couple the instrument 10 with the second component 200.

Figure 7A:
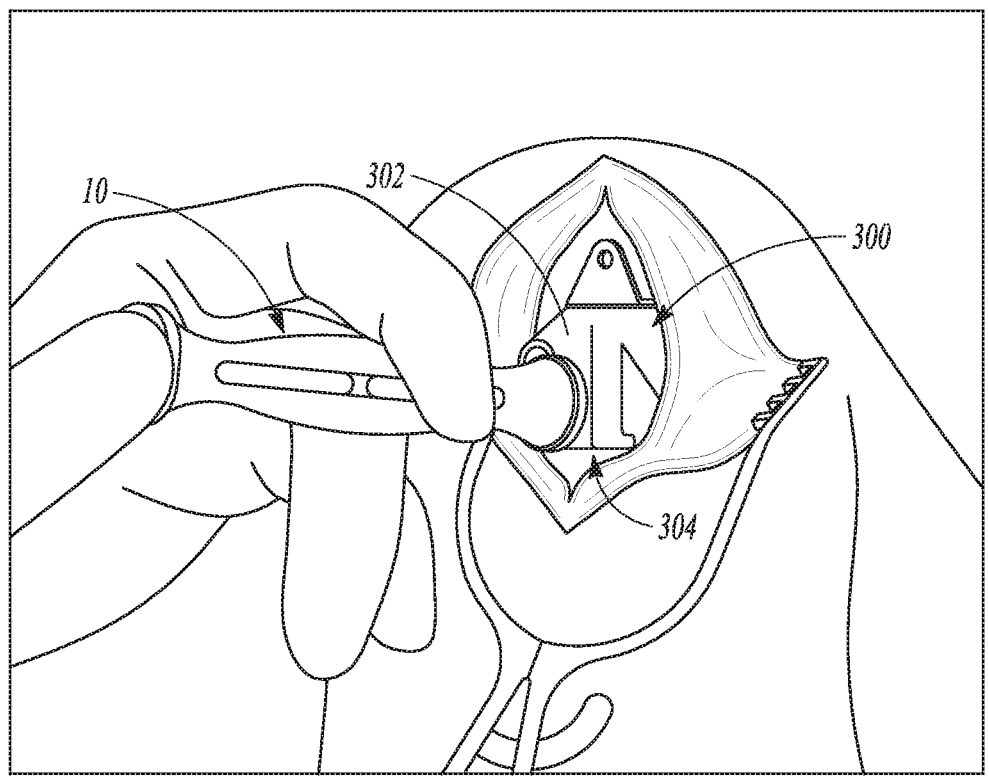
FIG. 7A is a perspective view of the instrument coupling with a femoral resection guide inserted in the knee joint of a patient according to an example of the present application.
Figure 7B:
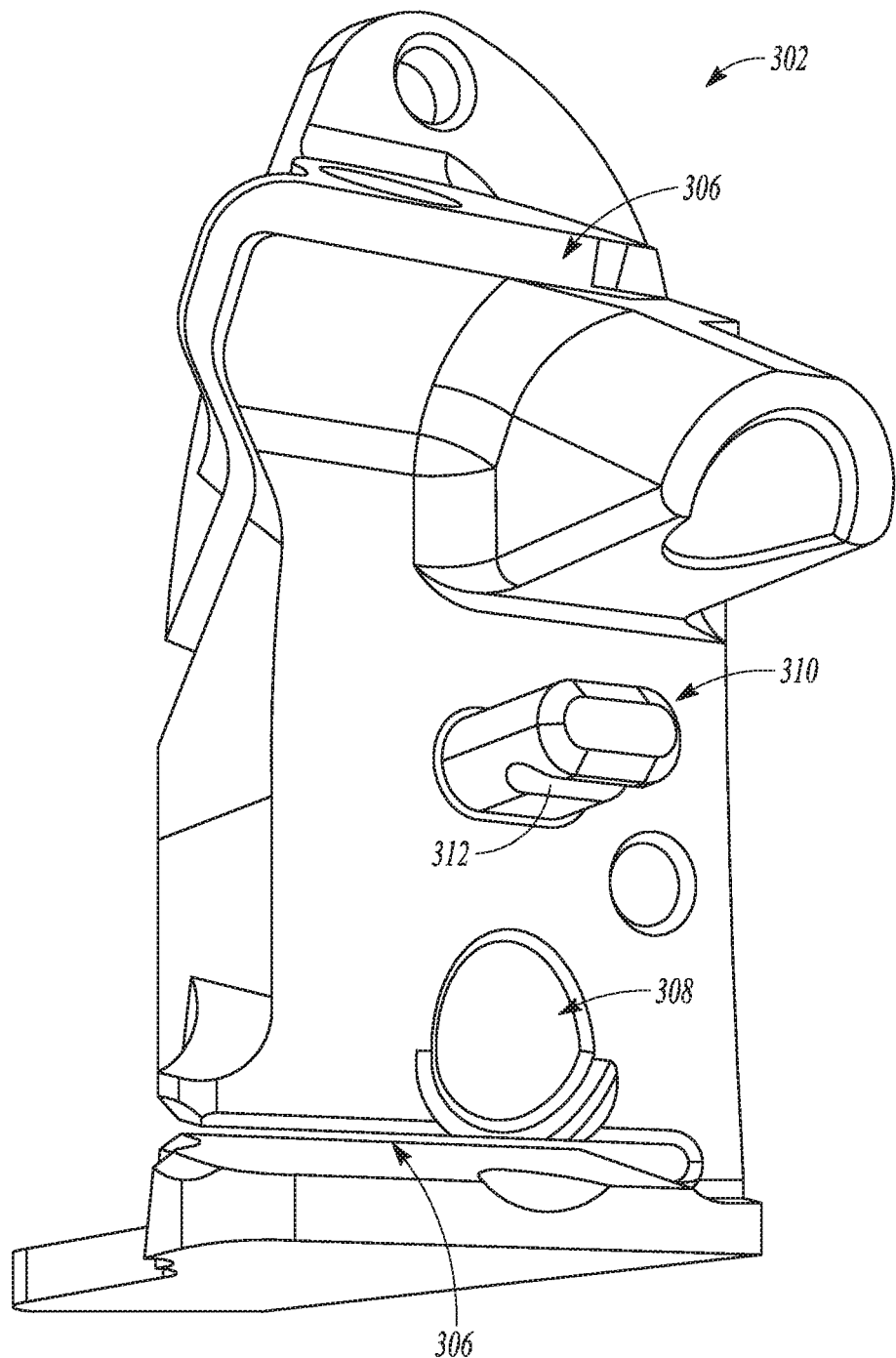
FIG. 7B is a perspective view of the femoral resection guide having a coupling feature configured to be received in the receptacle of the instrument according to an example of the present application.

FIG. 7A shows the instrument 10 coupling with a third component 300 comprising a femoral finishing cut guide 302 at the knee joint 304 of the patient. As shown in FIG. 7B, the femoral finishing guide 302 can be configured to mount to the femur of the patient and can have a number of cut slots 306 and peg holes 308 to aid in the performance of resection of the femur following the distal resection of the femur performed utilizing the guide and spacer block 202 discussed previously. Further details regarding the construction of the femoral finishing cut guide 302 can be found in co-pending U.S. application Ser. No. 15/203,370, filed on Jul. 6, 2016, and entitled "FEMORAL FINISHING GUIDE", the entire disclosure of which is incorporated herein by reference.

As shown in FIG. 7B, the second component 300 can have a projection 310 configured to insert in the receptacle of the instrument 10 (as shown in FIG. 7A). The projection 310 of the third component 300 can define a recess 312 configured to receive the detent 18 (FIG. 1) therein to couple the instrument 10 with the third component 300.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An instrument for at least one of mounting and removal of a component to or from bone during a knee procedure, the instrument comprising:
    a handle having a proximal end and a distal end and a longitudinal extent between the proximal end and the distal end;
    a body connected to the handle and extending distal of the distal end of the handle, the body defining a receptacle therein having an opening at a distal end portion of the instrument, wherein a most distal tip of the body comprises an engagement feature that forms a distally protruding curved surface of the body, wherein the engagement feature is configured to engage the bone and provide a proximal/distal stop for the instrument against the bone and is positioned distal of the opening to the receptacle, wherein the engagement feature forms a most distal end of the instrument;
    a plunger moveably disposed within the body and moveable between a first position and a second position;
    a detent moveable by the plunger such that with the plunger in the first position, at least a portion of the detent extends into the receptacle, and with the plunger in the second position the detent is recessed from the receptacle, wherein in the first position the detent engages a recess in the component for coupling the instrument thereto to facilitate at least one of mounting and removal of the component to or from bone during the knee procedure; and
    a collar disposed about at least a portion of the body and moveable relative to the body to operatively actuate the plunger from the first position to the second position;
    wherein the plunger defines a recess configured to receive the detent therein when the plunger is in the second position and the plunger has a ramp surface from the recess to a nose projection, and wherein the nose projection is configured to hold the at least the portion of the detent within the receptacle when the plunger is in the first position.

2. The apparatus of claim 1, further comprising a spring disposed within the body and configured to apply a force on the plunger that holds the plunger in the first position.

3. The apparatus of claim 2, further comprising a pin extending through at least a portion of the collar, the plunger and the body, wherein the pin is contacted by the spring and transfers the force to the plunger.

4. The apparatus of claim 3, wherein at least one of the collar and the body includes one or more slots configured to receive the pin, and wherein the one or more slots are configured to allow proximal and distal travel of the pin relative to the body.

5. The apparatus of claim 1, wherein the engagement feature is configured with curvatures along an engagement face in both a longitudinal direction and a transverse direction.

6. The apparatus of claim 1, wherein the instrument is reversible with respect to a longitudinal axis so as to dispose the engagement feature in a first orientation so as to be configured to make engagement with the bone and a second orientation so as to be configured to avoid contact with the bone.

7. An instrument for at least one of mounting and removal of a component to or from bone during a knee procedure, the instrument comprising:
   a body comprising a distal part of the instrument, the body defining a receptacle therein having an opening interfacing but recessed from a distal end of the instrument by an engagement feature configured to engage the bone and provide a proximal/distal stop for the instrument;
   a detent moveable within the body such that with the detent in a first position at least a portion of the detent extends into the receptacle and with the detent in a second position the detent is recessed from the receptacle; and
   an actuator configured to operatively actuate the detent from the first position to the second position;
   wherein the instrument is reversible with respect to a longitudinal axis so as to dispose the engagement feature in a first orientation so as to be configured to make engagement with the bone and a second orientation so as to be configured to avoid contact with the bone.

8. The instrument of claim 7, wherein the engagement feature is configured with curvatures along an engagement face in both a longitudinal direction and a transverse direction.

9. An instrument for at least one of mounting and removal of a component to or from bone during a knee procedure, the instrument comprising:
   a handle having a proximal end and a distal end and a longitudinal extent between the proximal end and the distal end;
   a body connected to the handle and extending distal of the distal end of the handle, the body defining a receptacle therein having an opening at a distal end portion of the instrument, wherein a most distal tip of the body comprises an engagement feature, wherein the engagement feature comprises a distally protruding curved surface of the body and is configured to engage the bone and provide a proximal/distal stop for the instrument against the bone, wherein the body is non-symmetrically shaped with respect to a longitudinal axis such that the engagement feature is positioned to one side of the longitudinal axis, and wherein the engagement feature is configured with curvatures along an engagement face in both a longitudinal direction and a transverse direction;
   a plunger moveably disposed within the body and moveable between a first position and a second position;
   a detent moveable by the plunger such that with the plunger in the first position, at least a portion of the detent extends into the receptacle, and with the plunger in the second position the detent is recessed from the receptacle;
   wherein the plunger defines a recess configured to receive the detent therein when the plunger is in the second position and the plunger has a ramp surface from the recess to a nose projection, and wherein the nose projection is configured to hold the at least the portion of the detent within the receptacle when the plunger is in the first position, wherein in the first position the detent engages a recess in the component for coupling the instrument thereto to facilitate at least one of mounting and removal of the component to or from bone during the knee procedure.

10. The instrument of claim 9, further comprising a collar moveable relative to the body to operatively actuate the plunger from the first position to the second position.

11. The instrument of claim 10, further comprising a spring disposed within the body and configured to apply a force on the plunger that holds the plunger in the first position.

12. The instrument of claim 11, further comprising a pin extending through at least a portion of the collar, the plunger and the body, wherein the pin is contacted by the spring and transfers the force to the plunger.

13. The instrument of claim 12, wherein at least one of the collar and the body includes one or more slots configured to receive the pin, and wherein the one or more slots are configured to allow proximal and distal travel of the pin relative to the body.

14. The instrument of claim 9, wherein the instrument is reversible with respect to a longitudinal axis so as to dispose the engagement feature in a first orientation so as to be configured to make engagement with the bone and a second orientation so as to be configured to avoid contact with the bone.

* * * * *